(12) United States Patent
Muñoz Muñoz

(10) Patent No.: US 9,999,197 B2
(45) Date of Patent: Jun. 19, 2018

(54) LETTUCE VARIETY NUN 6109 LTL

(71) Applicant: Nunhems B.V., Nunhem (NL)

(72) Inventor: Juan Francisco Muñoz Muñoz, Nunhem (NL)

(73) Assignee: Nunhems B.V., Nunhem (NL)

( * ) Notice: Subject to any disclaimer, the term of this patent is extended or adjusted under 35 U.S.C. 154(b) by 178 days.

(21) Appl. No.: 14/798,885

(22) Filed: Jul. 14, 2015

(65) Prior Publication Data

US 2015/0313171 A1  Nov. 5, 2015

(51) Int. Cl.
*A01H 5/12* (2018.01)
*A01H 4/00* (2006.01)
*A01H 1/02* (2006.01)

(52) U.S. Cl.
CPC .................. *A01H 5/12* (2013.01); *A01H 1/02* (2013.01); *A01H 4/005* (2013.01)

(58) Field of Classification Search
None
See application file for complete search history.

(56) References Cited

U.S. PATENT DOCUMENTS

| | | | | |
|---|---|---|---|---|
| 6,555,735 | B2 * | 4/2003 | Sarreal | A01H 5/12 |
| | | | | 435/410 |
| 7,321,078 | B1 * | 1/2008 | Knerr | A01H 5/12 |
| | | | | 435/410 |
| 7,427,699 | B1 * | 9/2008 | Skrsyniarz | A01H 5/12 |
| | | | | 435/410 |
| 8,076,539 | B2 * | 12/2011 | Knerr | A01H 5/12 |
| | | | | 435/410 |
| 9,198,396 | B2 * | 12/2015 | van Zee | A01H 5/12 |
| 2008/0222949 | A1 | 9/2008 | Bissonnette et al. | |
| 2013/0247243 | A1 * | 9/2013 | van Zee | A01H 5/12 |
| | | | | 800/265 |
| 2015/0272077 | A1 * | 10/2015 | Munoz Muñoz | A23K 10/30 |
| | | | | 800/260 |

FOREIGN PATENT DOCUMENTS

EP  1197137 A1  4/2002

OTHER PUBLICATIONS

Acquaah, Principles of Plant Genetics and Breeding, 2007, Blackwell Publishing, ISBN-13: 978-1-4051-3646-4.
U.S. Department of Agriculture, Agricultural Marketing Service, Objective Description of Variety, Lettuce (*Lactuca sativa* L.), http://www.ams.usda.gov/AMSv1.0/getfile?dDocName=stelprdc5069208.
Upov, Guidelines for the Conduct of Tests for Distinctness, Uniformity and Stability, Lettuce, TG/13/10 (Geneva, 2006), http://www.upov.int/en/publications/tg-rom/tg013/tg_13_10.pdf.
Teng, Whei-Lan, et al., HortScience. 1992, vol. 27(9), pp. 1030-1032.
Teng, Whei-Lan, et al., HortScience. 1993, vol. 28(6), pp. 669-671.
Xinrun, Zhang, et al., Journal of Genetics and Breeding, 1992, vol. 46(3), pp. 287-290.
Halmer, P. Commercial seed treatment technology. In: Seed technology and its biological basis. Eds: Black, M. and Bewley, J. D., 2000, pp. 257-286.
Hill, H.J., et al., HortScience, 2007, vol. 42(6), pp. 1436-1439.
Gonai, Takeru, et al., Journal of Experimental Botany, 2004, vol. 55(394), pp. 111-118.
Jackson, Louise, et al., University of California, Publication 7215 ISBN 978-1-60107-007-4.
Jackson, Louise, et al, University of California, Publication 7216 ISBN 978-1-60107-008-1.
Vos, Pieter, et al., 1995, Nucleic Acids Research, 1995, vol. 23:21, pp. 4407-4414.
Van Eeuwijk, F.A. and Law, Euphytica, 2004, vol. 137, pp. 129-137.
Brotman, Y., et al., Theor Appl Genet, 2002, vol. 104, pp. 1055-1063.
Allard, 1960, John Wiley & Sons, Inc.: Principles of plant breeding: 119-128, Library of Congress Catalog Card No. 60-14240 (voluminous book).
Dziechciarkova, M., et al, Plant Soil Environ., 2004, vol. 50:2, pp. 47-58.

* cited by examiner

*Primary Examiner* — Ashley K Buran

(57) ABSTRACT

The present invention relates to the field of *Lactuca sativa*, in particular to a new variety of lettuce designated NUN 6109 LTL as well as seeds and plants and heads or leaves thereof.

17 Claims, No Drawings

LETTUCE VARIETY NUN 6109 LTL

FIELD OF THE INVENTION

The present invention relates to the field of plant breeding. In particular, the invention provides for a new and distinct variety of lettuce designated NUN 6109 LTL (or "NUN6109" or "6109" or "NUN6109 LT" or NUN 6109 or NUN 06109 LTL).

All cultivated forms of lettuce belong to the highly polymorphic species *Lactuca sativa* that is grown for its edible head and leaves. *Lactuca sativa* is in the *Asteraceae* (Compositae) family. Lettuce is related to chicory, sunflower, aster, dandelion, artichoke and chrysanthemum. *L. sativa* is one of about 300 species in the genus *Lactuca*.

Fresh lettuce is available in the United States year-round although the greatest supply is from May through October. For planting purposes, the lettuce season is typically divided into three categories, early, mid and late, with the coastal areas planting from January to August, and the desert regions planting from August to December. Fresh lettuce is consumed nearly exclusively as fresh, raw product and occasionally as a cooked vegetable.

The development of commercial lettuce cultivars requires the development of lettuce varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the inbred lines or hybrids from these crosses are evaluated to determine which have commercial potential.

Lifestyles change and the demand from restaurants and catering firms for colorful and interesting garnish for sandwiches and ready-to-use processed salads continue to rise. As a result, there is a demand for breeding companies to develop new varieties with specific shapes of leaves, specific average size of leaves, glossiness, prominent color and a wide variety of texture, as well as good yield.

SUMMARY OF THE INVENTION

In one aspect of the invention, a seed of new Cos/Romaine lettuce variety NUN 6109 LTL, wherein representative seed of said variety having been deposited under Accession Number NCIMB 43022.

In another aspect the invention provides for a variety of *Lactuca sativa* NUN 6109 LTL. The invention also provides for a plurality of seeds of the new variety, plants produced from growing the seeds of the new variety NUN 6109 LTL, and progeny of any of these. Especially, progeny retaining one or more (or all) of the "distinguishing characteristics" or one or more (or all) of the physiological and morphological characteristics of NUN 6109 LTL referred to herein, are encompassed herein as well as methods for producing these.

In one aspect, such progeny have all the physiological and morphological characteristics of lettuce variety NUN 6109 LTL when grown under the same environmental conditions. In another aspect such progeny have all the physiological and morphological characteristics as listed in Table 1 as lettuce variety NUN 6109 LTL when measured under the same environmental conditions (i.e. evaluated at significance levels of 1%, 5% or 10% significance, which can also be expressed as a p value).

In another aspect a plant of the invention or said progeny plants has/have 3, 4, 5, 6, 7, 8, or more, or all of the following (average) characteristics in addition to 1, 2, 3, 4, or more or all of the distinguishing characteristics: 1) an average length/width index x10 of fourth leaf of about 26, e.g. 25, 26, 27 or 28; 2) an average head weight of mature plant of about 594 g, e.g. 585, 590, 595, 600, 610 or 620 g; 3) an average diameter of core at base of head of about 28 mm, e.g. 26, 27, 28, 29 or 30 mm; 4) an average core height from base of head to apex of about 43 mm, e.g. 40, 41, 42, 43, 44, 45 or 46 mm; 5) an average spread of frame leaves of mature plant of about 31 cm, e.g. 28, 29, 30, 31, 32, 33, 34 or 35 cm; 6) an average head size class of type 2 (medium); 7) an average ratio of spread of frame leaves of about 1.1, e.g. 1.05; 1.06; 1.07; 1.08; 1.09; 1.10; 1.11; 1.12; 1.13; 1.14; 1.15; or 1.16; 8) average undulations of the apical margin of the mature leaf of type 3 (strong); 9) strong blistering of the mature leaf.

In another aspect a plant of the invention has in addition to the 1, 2, 3, 4 or more or all of the above-cited distinguishing characteristics, 3, 4, 5, 6, 7, 8, or more, or all of the other (average) characteristics as listed in Table 1.

Further, a lettuce head produced on a plant grown from these seeds is provided.

In yet another embodiment of the invention, a plant having one, two or three physiological and/or morphological characteristics which are different from those of NUN 6109 LTL and which otherwise has all the physiological and morphological characteristics of NUN 6109 LTL as listed in Table 1, wherein a representative sample of seed of variety NUN 6109 LTL has been deposited under Accession Number NCIMB 43022, is provided.

Further, a vegetatively propagated or regenerated plant of variety NUN 6109 LTL, or a part thereof, is provided having all the morphological and physiological characteristics of NUN 6109 LTL when grown under the same environmental conditions.

Also a plant part derived from variety NUN 6109 LTL is provided, wherein said plant part is selected from the group consisting of: head, leaf or leaves, fruit, pollen, ovule, cell, part of a leaf, petioles, shoots or parts thereof, stems or parts thereof, vines or parts thereof, roots or parts thereof, cuttings, seeds, hypocotyl, cotyledon, flowers or parts thereof, scion, stock, rootstock and flower. Heads are particularly important plant parts.

Definitions

All patent and non-patent literatures cited herein are incorporated by reference in their entireties.

"Lettuce" refers herein to plants of the species *Lactuca sativa* L.

"Cultivated lettuce" refers to plants of *Lactuca sativa* i.e. varieties, breeding lines or cultivars of the species *L. sativa* as well as crossbreds thereof, or crossbreds with other *Lactuca sativa* species, or even with other *Lactuca* species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Lactuca sativa*, comprising, for example *L. virosa* or *L. serriola*, and other related species.

The terms "NUN 6109 LTL", "lettuce plant designated NUN 06524", "NUN 06524" or "variety designated NUN 6109 LTL" are used interchangeably herein and refer to a lettuce plant of variety NUN 6109 LTL, representative seed of which having been deposited under Accession Number NCIMB 43022.

"USDA descriptors" are the plant variety descriptors described for lettuce in the "Objective description of Variety—Lettuce (Lactuca sativa L.)", as published by U.S. Department of Agriculture, Agricultural Marketing Service, Science and Technology, Plant Variety Protection Office, Beltsville, Md. 20705 and which can be downloaded from the world wide web at ams.usda.gov/ under AMSv1.0/getfile?dDocName=stelprdc5069208.

"UPOV descriptors" are the plant variety descriptors described for lettuce in the "Guidelines for the Conduct of Tests for Distinctness, Uniformity and Stability," TG/013/10 (Geneva 2006, last updated Mar. 20, 2013), as published by UPOV (International Union for the Protection of New Varieties and Plants) and which can be downloaded from the world wide web at upov.int/ under edocs/tgdocs/en/tg013.pdf and is herein incorporated by reference in its entirety. Likewise, "UPOV methods" to determine specific parameters for the characterization of lettuce are described at upov.int.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Graben 8, D-97877 Wertheim, Article-No.: Art62-00008 EAN-Nr.: 4250193402112).

As used herein, the term "plant" includes the whole plant or any parts or derivatives thereof, preferably having the same genetic makeup as the plant from which it is obtained, such as plant organs (e.g. harvested or non-harvested heads or leaves or packages comprising a plurality of leaves and/or heads of NUN 6109 LTL), plant cells, plant protoplasts, plant cell tissue cultures or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, fruits, flowers, leaves, heads, seeds, clonally propagated plants, roots, stems, vines, root tips, grafts, scions, rootstocks, parts of any of these and the like. Also any developmental stage is included, such as seedlings, cuttings prior or after rooting, mature and/or immature plants or mature and/or immature leaves.

"Tissue Culture" refers to a composition comprising isolated cells of the same or a different type or a collection of such cells organized into parts of a plant. Tissue culture of various tissues of lettuce and regeneration of plants therefrom is well known and widely published (see, e.g., Teng et al., HortScience. 1992, 27(9): 1030-1032 Teng et al., HortScience. 1993, 28(6): 669-1671, Zhang et al., Journal of Genetics and Breeding. 1992, 46(3): 287-290).

"Cotyledon" refers to one of the first leaves of the embryo of a seed plant; typically one or more in monocotyledons, two in dicotyledons and two or more in gymnosperms.

"Head" as used herein refers to lettuce heads, i.e., the plant without the root system, for example substantially all harvested leaves. Encompassed are immature leaves (e.g. "baby leaf") and mature leaves, as well as "loose leaf" and stem types.

The "base" of a plant is the part of a lettuce plant where the leaves are attached to the root system of the plant.

"Core length" of the internal lettuce stem is measured from the base of the cut and trimmed head to the tip of the stem.

"Head weight" refers to the mean weight of saleable lettuce head, cut and trimmed to market specifications.

"Head diameter" refers to the mean diameter of the cut and trimmed head, sliced vertically, and measured at the widest point perpendicular to the stem.

"Head height" refers to the mean height of the cut and trimmed head, sliced vertically, and measured from the base of the cut stem to the leaf tip.

"Core Length to Head Diameter Ratio (CLHD Ratio)" refers to the mean core length/head diameter ratio. It is calculated by dividing the mean core length with the mean head diameter. This is an indication of the head shape and of the ability of a lettuce plant to reduce the amount of surface which is on or close to the ground.

"Harvested plant material" refers herein to plant parts (e.g., leaves or heads detached from the whole plant) which have been collected for further storage and/or further use.

"Harvested seeds" refers to seeds harvested from a line or variety, e.g., produced after self-fertilization or cross-fertilization and collected.

"Yield" means the total weight of all lettuce heads or leaves harvested per hectare of a particular line or variety. It is understood that "yield" expressed as weight of all lettuce heads or leaves harvested per hectare can be obtained by multiplying the number of plants per hectare times the "yield per plant".

"Marketable yield" means the total weight of all marketable lettuce heads or leaves harvested per hectare of a particular line or variety, i.e. lettuce heads or leaves suitable for being sold for fresh consumption, having good color, glossiness size and texture and no or very low levels of deficiencies.

"Ground" refers to the surrounding of the aerial tissues of a lettuce plant in which it is grown, or which is placed on the growing medium (e.g. a foil covering the growing medium such as soil but which does not cover the aerial plant, e.g., there is a hole in the foil through which the lettuce plant is growing).

A plant having "all the physiological and morphological characteristics" of a referred-to-plant means a plant having the physiological and morphological characteristics of the referred-to-plant when grown under the same environmental conditions; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7, 8, 9 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.). Alternatively, a plant having "essentially all the physiological and morphological characteristics" of a referred-to-plant means a plant having all the characteristics as listed in Table 1 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 when grown under the same environmental conditions as a referred-to-plant (e.g. a plant from which it was derived such as the progenitor plant, the parent, the recurrent parent, the plant used for tissue- or cell culture, etc.).

For NUN 6109 LTL the distinguishing characteristics are 1) average length/width index x10 of fourth leaf; 2) average head weight of mature plant; 3) average diameter of core at base of head; 4) average core height from base of head to apex; 5) average spread of frame leaves of mature plant; 6) average head size class; 7) average ratio of spread of frame leaves; 8) average undulation of the apical margin of the mature leaf; 9) mature leaf blistering).

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 when grown under the same environmental conditions that distinguish NUN 6109 LTL from the most similar varieties (such as variety GREEN TOWERS), such as but not limited to average head weight, leaf size, shape, color, glossiness and texture, maturity, or bolting.

"Distinguishing characteristics" or "distinguishing morphological and/or physiological characteristics" refers herein the characteristics which are distinguishing between NUN 6109 LTL and other lettuce varieties, such as GREEN TOWERS, when grown under the same environmental conditions, especially the following characteristics 1) an average length/width index x10 of fourth leaf of about 26 cm (e.g. between 26-4% and 26+4%); 2) an average head weight of mature plant of about 594 g (e.g. between 594-5% and 594+5% g); 3) an average diameter of core at base of head of about 28 mm (e.g. between 28-5% and 28+5% mm); 4) an average core height from base of head to apex of about 43 mm (e.g. between 43-5% and 43+5% mm); 5) an average spread of frame leaves of mature plant of about 31 cm (e.g. between 31-5% and 31+5% cm); 6) an average head size class of type 2 (medium); 7) an average ratio of spread of frame leaves of about 1.1 (e.g. between 0.99 and 1.21); 8) strong average undulations of the apical margin of the mature leaf; 9) strong blistering of the mature leaf.

In one aspect, the distinguishing characteristics further include at least one, two, three or more (or all) of the characteristics listed in Table 1. All numerical distinguishing characteristics are statistically significantly different at p≤0.05.

Thus, a lettuce plant "comprising the distinguishing characteristics of NUN 6109 LTL" refers herein to a lettuce plant which does not differ significantly from NUN 6109 LTL in characteristics 1) to 5) above. In a further aspect the lettuce plant further does not differ significantly from NUN 6109 LTL in one or more, or all characteristics 6) to 9) as mentioned above. In yet a further aspect the lettuce plant further does not differ in at least one, two, three, four, five or six (or all) characteristics selected from the characteristics listed in Table 1. In still another aspect the lettuce plant does not differ in any of the distinguishing characteristics 1) to 9) listed above.

The physiological and/or morphological characteristics mentioned above are commonly evaluated at significance levels of 1%, 5% or 10% if they are numerical, or for identical type if not numerical, when measured under the same environmental conditions. For example, a progeny plant of NUN 6109 LTL may have one or more (or all) of the essential physiological and/or morphological characteristics of NUN 6109 LTL listed in Table 1, as determined at the 5% significance level (i.e. p≤0.05) when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Progeny" as used herein refers to plants derived from a plant designated NUN 6109 LTL. Progeny may be derived by regeneration of cell culture or tissue culture or parts of a plant designated NUN 6109 LTL or selfing of a plant designated NUN 6109 LTL or by producing seeds of a plant designated NUN 6109 LTL. In further embodiments, progeny may also encompass plants derived from crossing of at least one plant designated NUN 6109 LTL with another lettuce plant of the same or another variety or (breeding) line, or wild Lactuca plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

"Plant line" is for example a breeding line which can be used to develop one or more varieties. Progeny obtained by selfing a plant line has the same phenotype as its parents.

"Inbred variety" refers to an inbred (nearly homozygous) line or seeds thereof. For example, the (nearly homozygous) plant is repeatedly (e.g. at least 6) self-pollinated or the (nearly homozygous) female parent is repeatedly pollinated with pollen of the same plant line to produce inbred seeds on the female parent.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one lettuce line or variety to another.

"Crossing" refers to the mating of two parent plants. Equally "Cross-pollination" refers to fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Selfing" refers to self-pollination of a plant, i.e., the transfer of pollen from the anther to the stigma of the same plant. Lettuce is an obligate self-pollination species, which means that pollen is shed before stigma emergence, assuring 100% self-fertilization.

In order to optimize crossing, a method of misting may be used to wash the pollen off, prior to fertilization to assure crossing or hybridization.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a vegetative propagation.

"Locus" (plural loci) refers to the specific location of a gene or DNA sequence on a chromosome. A locus may confer a specific trait.

"Genotype" refers to the genetic composition of a cell or organism.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

The terms "gene converted" or "conversion plant" in this context refer to lettuce plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a lettuce variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a lettuce plant by transformation. A plant comprising a transgene stably integrated into its genome is referred to as "transgenic plant".

"Substantially equivalent" refers to a characteristic that, when compared, does not show a statistically significant difference (e.g., p=0.05) from the mean.

"Average" refers herein to the arithmetic mean.

"First water date" refers to the date the seed first receives adequate moisture to germinate. This can and often does equal the planting date.

"Maturity date" refers to the stage when the plants are of full size or optimum weight, in marketable form or shape to be of commercial or economic value. This is also the time point when measuring parameters of "mature" leaves.

The term "mean" refers to the arithmetic mean of several measurements. The skilled person understands that the appearance of a plant depends to some extent on the growing conditions of said plant. Thus, the skilled person will know typical growing conditions for lettuce of the types described herein. The mean, if not indicated otherwise within this application, refers to the arithmetic mean of measurements on at least 10 different, randomly selected plants of a variety at a required developing stage (e.g., fourth leaf or mature).

DETAILED DESCRIPTION

The present invention relates to a lettuce (*Lactuca sativa*) variety, designated NUN 6109 LTL. Lettuce variety designated NUN 6109 LTL is of the Cos/Romaine Type (USDA sheet). NUN 6109 LTL—when compared to check variety GREEN TOWERS—has a higher average length/width index x10 of fourth leaf; a lower average head weight; a smaller average diameter of core at base of head; a smaller average core height from base of head to apex; a lower average spread of frame leaves of mature plant; an average head size class of type 2 (medium) instead of type 3 (large); a lower average ratio of spread of frame leaves; average undulations of the apical margin of the mature leaf of type 3 (strong) instead of type 2 (moderate); blistering of the mature leaf of type 3 (strong) instead of type 2 (moderate).

Also encompassed by the present invention are progeny plants having all but 1, 2, or 3 of the morphological and/or physiological characteristics of NUN 6109 LTL and methods of producing plants in accordance with the present invention.

A lettuce plant of NUN 6109 LTL differs from the most similar comparison variety GREEN TOWERS in one or more characteristics (referred herein to as "distinguishing characteristics" or "distinguishing morphological and/or physiological characteristics" (or essential physiological and/or morphological characteristics) selected from:

1) NUN 6109 LTL has an average length/width index x10 of fourth leaf that is at least 5%, e.g. 5, 6, 7, 8, 8.4, 9, 10, 11% or even 15% higher than GREEN TOWERS;
2) NUN 6109 LTL has an average head weight of mature plant that is at least 7%, e.g. 7, 8, 9, 10, 11% or even 11.7% lower than GREEN TOWERS;
3) NUN 6109 LTL has an average diameter of core at base of head that is at least 5%, e.g. 6, 8, 10, 12, 14, 15, 16, 17% or even 17.6% lower than GREEN TOWERS;
4) NUN 6109 LTL has an average core height from base to head of apex that is at least 10%, e.g. 15, 20, 24, 26, 28, 29, 30% or even 30.6% lower than GREEN TOWERS;
5) NUN 6109 LTL has an average spread of frame leaves that is at least 10%, e.g. 15, 18, 20, 21, 22, 23, 24, 25, 26, or even 26.2% smaller than GREEN TOWERS;

6) NUN 6109 LTL has an average head size class of type 2 (medium) whereas GREEN TOWERS has an average head size class of type 3 (large);
7) NUN 6109 LTL has a ratio of spread of frame leaves at core that is at least 5%, e.g. 6, 7, 8% or even 8.3% lower than GREEN TOWERS;
8) NUN 6109 LTL has average undulations of the apical margin of the mature leaf of type 3 (strong) whereas GREEN TOWERS has average undulations of the apical margin of the mature leaf of type 2 (moderate);
9) NUN 6109 LTL has a mature leaf blistering of type 3 (strong), whereas GREEN TOWERS has a mature leaf blistering of type 2 (moderate).

In yet another embodiment of the invention, NUN 6109 LTL has an average leaf width of fourth leaf that is at least 5%, e.g. 6, 7, 8, 9, 10% or even 10.6% higher than GREEN TOWERS. In also another embodiment of the invention, NUN 6109 LTL has an average plant leaf length of fourth leaf that is at least 12%, e.g. 13, 14, 15, 16, 17, 18% or even 19.1% higher than GREEN TOWERS.

In still another embodiment, NUN 6109 LTL has an average plant height that is at least 5%, e.g. 6, 7, 8, 9, 10% or even 11.3% lower than GREEN TOWERS.

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the lettuce variety designated NUN 6109 LTL wherein a representative sample of seeds of said variety was deposited under the Budapest Treaty, with Accession number NCIMB 43022.

Seeds of NUN 6109 LTL are obtainable by, e.g., growing plants from the seeds deposited under Accession number NCIMB 43022 and allowing e.g., self-pollination and/or cross-pollination and collecting seeds from the resulting plants. The resultant NUN 6109 LTL seeds can be grown to produce plants designated NUN 6109 LTL. Moreover, a seed designated NUN 6109 LTL also refers to a seed wherein the plant grown therefrom shows all or all but 1, 2, 3, 4, 5 physiological and morphological characteristics of NUN 6109 LTL. Seeds of NUN 6109 LTL are also obtainable by vegetative propagation from plant cells or tissue of a plant grown from seeds of NUN 6109 LTL. In one embodiment a plurality of NUN 6109 LTL seeds are packaged into small and/or large containers (e.g., bags, cartons, cans, etc.). The seeds may be disinfected, primed and/or treated with various compounds, such as seed coatings or crop protection compounds.

Seed priming and pelleting treatments can be used to improve the performance of seed of NUN 6109 LTL. Seeds are typically cleaned and disinfected before further treatment. Pelleting creates round or rounded shapes, which are easily sown with modern sowing machines (Halmer, P. 2000. Commercial seed treatment technology. In: Seed technology and its biological basis. Eds: Black, M. and Bewley, J. D., pages 257-286). A pelleting mixture typically contains seeds and at least glue and filler material. The latter could be, for example, clay, mica, chalk or cellulose. Seed pelleting can be combined with film coating. In addition, certain additives can be included to improve particular properties of the pellet, e.g., a seed treatment formulation comprising at least one insecticidal, acaricidal, nematicidal, herbicidal, biological active, growth promoting or fungicidal ingredient can be added directly into the pelleting mixture or in separate layers. A seed treatment formulation can include one of these types of compounds only, a mixture of two or more of the same type of compounds.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds (Halmer, P. 2000. Commercial seed treatment technology. In: Seed technology and its biological basis. Eds: Black, M. and Bewley, J. D., pages 257-286). Besides the formulation, the coating mixture generally also contains other ingredients such as water, glue (typically a polymer), filler materials, pigments and certain additives to improve particular properties of the coating. Several coatings can be combined on a single seed. In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'mini-pellet'.

Seeds may also be primed. Of all the commercially planted vegetable seeds, lettuce is the most often primed. Priming is a water-based process that is performed on seeds to increase uniformity of germination and emergence from the soil, and thus enhance vegetable stand establishment. Priming decreases the time span between the emergence of the first and the last seedlings. Methods for priming lettuce seeds are well known in the art (see, e.g., Hill et al HortScience 42(6): 1436, 2007).

Also provided are plants of lettuce variety NUN 6109 LTL, or a head or leaves or another plant part thereof, produced from seeds, wherein a representative sample of said seeds has been deposited under the Budapest Treaty, with Accession Number NCIMB 43022. Also included is a cell culture or tissue culture produced from such a plant. It is understood that such tissue or cell culture comprising cells or protoplasts from the plant of the invention can be obtained from a plant part selected from the group consisting of embryos, meristems, cotyledons, hypocotyl, pollen, leaves, heads, anthers, roots, root tips, pistil, petiole, flower, fruit, seed, stem and stalks. In one embodiment a plant regenerated from such a cell or tissue culture said plant expressing all the morphological and physiological characteristics of NUN 6109 LTL.

In one embodiment the invention provides a lettuce plant regenerated from the tissue or cell culture of NUN 6109, wherein the plant has all of the physiological and morphological characteristics of NUN 6109 LTL as listed in Table 1 when determined at the 5% significance level. In another embodiment, the invention provides a lettuce plant regenerated from the tissue or cell culture of NUN 6109 LTL, wherein the plant has all of the physiological and morphological characteristics of NUN 6109 LTL when determined at the 5% significance level.

Plants of NUN 6109 LTL can be produced by seeding directly in the ground (e.g., soil such as soil in a field) or by germinating the seeds in controlled environment conditions (e.g., greenhouses) and then transplanting the seedlings into the field (see, e.g., Gonai et al., J. of Exp. Bot., 55(394): 111, 2004; Louise Jackson et al, Publication 7215 ISBN 978-1-60107-007-4 and Publication 7216 ISBN 978-1-60107-008-1 and the world wide web at "anrcatalog.ucdavis.edu" search: lettuce for cultivation, harvesting, handling and postharvest methods commonly used). It may also be grown in tunnels. Moreover, NUN 6109 LTL can be grown in hydroponic cultures as described in, e.g., US 2008/0222949, and the skilled person is familiar with various types of hydroponic cultures. Alternatively, seed of NUN 6109 LTL may be grown on peat block for use as root ball lettuce. Furthermore, NUN 6109 LTL may be combined with 1, 2 or 3 different lettuce varieties to be grown as "composite lettuce" (see, e.g., EP 1 197 137 A1).

In another aspect, the invention provides for a lettuce plant of variety NUN 6109 LTL, a representative sample of seed from said variety has been deposited under the Budapest Treaty, with Accession number NCIMB 43022.

In other aspects, the invention provides for a lettuce head or leaves or parts thereof of lettuce variety NUN 6109 LTL, or a plant part, such as pollen, flowers, shoots or cuttings of variety NUN 6109 LTL or parts thereof.

In one embodiment a plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Lettuce (unless indicated otherwise), when grown under the same environmental conditions):
1) NUN 6109 LTL has an average length/width index x10 of fourth leaf of about 26, e.g. between 24 and 28, or preferably between 25 and 27, or even between 26.5 and 27.5.
2) NUN 6109 LTL has an average head weight of mature plant of about 594 g, e.g. between 580 and 610 g, or preferably between 585 and 604 g, or even between 589 and 599 g.;
3) NUN 6109 LTL has an average diameter of core at base of head of about 28 mm, e.g. between 26 and 30 mm, or preferably between 27 and 29 mm, or even between 27.5 and 28.5 mm;
4) NUN 6109 LTL has an average core height from base of head to apex of about 43 mm, e.g. between 40 and 46 mm, or preferably between 41 and 45 mm, or even between 42 and 44 mm;
5) NUN 6109 LTL has an average spread of frame leaves of mature plant of about 31 cm, e.g. between 28 and 34 cm, or preferably between 29 and 33 cm, or even between 30 and 32 cm;
6) NUN 6109 LTL has an average head size class of type 2 (medium);
7) NUN 6109 LTL has an average ratio of spread of frame leaves of about 1.1, e.g. between 1.0 and 1.2, or preferably between 1.05 and 1.15, or even between 1.13 and 1.18;
8) NUN 6109 LTL has average undulations of the apical margin of the mature leaf of type 3 (strong);
9) NUN 6109 LTL has strong blistering of the mature leaf.

In still another aspect the invention provides a method of producing a lettuce plant, comprising crossing a plant of lettuce variety NUN 6109 LTL with a second lettuce plant one or more times, and selecting progeny from said crossing.

In yet another aspect the invention provides a method of producing a lettuce plant, comprising selfing a plant of lettuce variety NUN 6109 LTL one or more times, and selecting progeny from said selfing.

In other aspects, the invention provides for progeny of variety NUN 6109 LTL such as progeny obtained by further breeding NUN 6109 LTL. Further breeding NUN 6109 LTL includes selfing NUN 6109 LTL one or more times and/or cross-pollinating NUN 6109 LTL with another lettuce plant or variety one or more times. In particular, the invention provides for progeny that retain all the essential morphological and physiological characteristics of NUN 6109 LTL or that retain one or more (e.g. 1) to 5) or 1) to 9) or all) of the distinguishing characteristics of the lettuce type described further above, or, in another embodiment, progeny that retain all morphological and physiological characteristics of NUN 6109 LTL as listed in Table 1, when grown under the same environmental conditions, which is determined at the 5% significance level for numerical characteristics. In another aspect, the invention provides for vegetative reproductions of the variety and plants having all but 1, 2, or 3 of the physiological and morphological characteristics of NUN 6109 LTL (e.g. as listed in Table 1).

The morphological and/or physiological differences between plants according to the invention, i.e. NUN 6109 LTL or progeny thereof, or plants having all but 1, 2, or 3 of the physiological and morphological characteristics of NUN 6109 LTL (as listed in Table 1); and other known varieties can easily be established by growing NUN 6109 LTL next to the other varieties (in the same field, under the same environmental conditions), preferably in several locations which are suitable for said lettuce cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby maturity, leaf shape, size and texture, leaf color and glossiness, bolt shape, surface and length, flower size and color, head weight, disease resistance, insect resistance and resistance to physiological stress can be measured and directly compared for species of Lactuca sativa.

The morphological and physiological characteristics (and distinguishing characteristics) of NUN 6109 LTL, are provided in the Examples, in Table 1. Encompassed herein are also plants derivable from NUN 6109 LTL (e.g. by selfings and/or crossing and/or backcrossing with NUN 6109 LTL and/or progeny thereof) comprising all the physiological and morphological characteristics of NUN 6109 LTL listed in Table 1 as determined at the 5% significance level for numerical characteristics or identical for non-numerical characteristics when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of heads or leaves can be compared, such as cold storage holding quality, post-harvest leaf crispyness and leaf browning or pinking after cutting can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (world wide web at rhs.org.uk/Plants/RHS-Publications/RHS-colour-charts).

In a preferred embodiment, the invention provides for lettuce heads or leaves of variety NUN 6109 LTL, or a part of the head or a leaf or a part of a leaf. In another embodiment, the invention provides for a container comprising or consisting of a plurality of harvested lettuce heads or leaves of NUN 6109 LTL, or progeny thereof, or a derived variety.

In yet a further embodiment, the invention provides for a method of producing a new lettuce plant. The method comprises crossing a plant of the invention NUN 6109 LTL, or a plant comprising all but 1, 2, or 3 of the morphological and physiological characteristics of NUN 6109 LTL (as listed in Table 1), or a progeny plant thereof, either as male or as female parent, with a second lettuce plant (or a wild relative of lettuce) one or more times, and/or selfing a lettuce plant according to the invention i.e. NUN 6109 LTL, or a progeny plant thereof, one or more times, and selecting progeny from said crossing and/or selfing. The second lettuce plant may for example be a line or variety of the species *Lactuca sativa*, or other *Lactuca* species or even other *Asteraceae* species.

Progeny are a later generation (of seeds) produced from the first cross of NUN 6109 LTL the F1 hybrid with another plant (F1) or with itself (S1), or any further generation produced by crossing and/or selfing (F2, F3, F4, etc.; S2, S3, S4, etc) and/or backcrossing (BC2, BC3, etc.) one or more selected plants of the F1 and/or S1 and/or BC2 generation (or plants of any further generation, e.g. the F3) with another lettuce plant (and/or with a wild relative of lettuce). Progeny may have all the physiological and morphological characteristics of lettuce variety NUN 6109 LTL when grown under the same environmental conditions and/or progeny may have (be selected for having) one or more of the distinguishing characteristics of lettuce of the invention. Using common breeding methods such as backcrossing or recurrent selection, one or more specific characteristics may be introduced into NUN 6109 LTL, to provide or a plant comprising all but 1, 2, or 3 or more of the morphological and physiological characteristics of NUN 6109 LTL (as listed in Table 1).

The invention provides for methods of producing plants which retain all the morphological and physiological characteristics of NUN 6109 LTL. The invention provides also for methods of producing a plant comprising all but 1, 2, or 3 or more of the morphological and physiological characteristics of NUN 6109 LTL (e.g. as listed in Table 1), but which are still genetically closely related to NUN 6109 LTL. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 6109 LTL if its DNA fingerprint is at least 80%, 90%, 95% or 98% identical to the fingerprint of NUN 6109 LTL. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (van Eeuwijk and Law (2004), Euphytica 137: 129-137). See also the Guidelines on Essentially Derived Varieties for lettuce published by the ISF (see website 'Worldseed', 'EDV'), where the technical protocol for assessing the Jaccard index is outlined.

The invention also provides plants and varieties obtained by these methods. Plants may be produced by crossing and/or selfing, or alternatively, a plant may simply be identified and selected amongst NUN 6109 LTL plants, or progeny thereof, e.g. by identifying a variant within NUN 6109 LTL or progeny thereof (e.g. produced by selfing) which variant differs from NUN 6109 LTL in one, two or three of the morphological and/or physiological characteristics (e.g. in one, two or three distinguishing characteristics), e.g. those listed in Table 1 or others. In one embodiment the invention provides a lettuce plant having a Jaccard's Similarity index with NUN 6109 LTL of at least 0.8, e.g. at least 0.85, 0.9, 0.95, 0.98 or even at least 0.99.

By crossing and/or selfing also (one or more) single traits may be introduced into the variety of the invention i.e. NUN 6109 LTL (e.g., using backcrossing breeding schemes), while retaining the remaining morphological and physiological characteristics of NUN 6109 LTL and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 6109 LTL by breeding with NUN 6109 LTL.

Any pest or disease resistance genes may be introduced into a plant according to the invention, i.e. NUN 6109 LTL, progeny thereof or into a plant comprising all but 1, 2, or 3 or more of the morphological and physiological characteristics of NUN 6109 LTL (e.g. as listed in Table 1). Resistance against one or more of the following diseases is preferably introduced into plants of the invention: Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows. Resistance against one or more of the following pests is preferably present or introduced into plants of the invention: *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt) resistance. Other resistance genes, against pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria or lettuce pests may also be introduced. In one embodiment resistance against *Nasonovia ribisnigri* biotype Nr:0 and/or Nr:1 is introduced into NUN 6109 LTL. Other resistance genes, against pathogenic viruses, fungi, bacteria, nematodes, insects or other pests may also be introduced.

Also, any resistance genes to physiological stresses may be introduced into a plant according to the invention, i.e. NUN 6109 LTL, progeny thereof or into a plant comprising all but 1, 2, or 3 or more of the morphological and physiological characteristics of NUN 6109 LTL (e.g. as listed in Table 1). Resistance against one or more of the following is preferably introduced into plants of the invention: Tipburn, Heat, Drought, Cold, Salt and/or Brown rob (Rib discoloration/rib blight).

Thus, invention also provides a method for developing a lettuce plant in a lettuce breeding program, using a lettuce plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 6109 LTL or progeny thereof, or a plant comprising all but 1, 2, or 3 or more of the morphological and physiological characteristics of NUN 6109 LTL (e.g. as listed in Table 1), with a different lettuce plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Brotman et al., Theor Appl Genet (2002) 104:1055-1063). Pedigree selection, also known as the "Vilmorin system of selection," is described in, e.g., Allard, 1960, John Wiley & Sons, Inc.: Principles of plant breeding: 119-128, Library of Congress Catalog Card Number: 60-14240. For breeding methods in general see Principles of Plant Genetics and Breeding, 2007, George Acquaah, Blackwell Publishing, ISBN-13: 978-1-4051-3646-4.

Thus, in one aspect a method for developing a lettuce plant in a lettuce breeding program is provided, using a lettuce plant of the invention, or its parts, as a source of plant breeding material. Suitable plant breeding techniques are recurrent selection, backcrossing, pedigree breeding, line selection, mass selection, mutation breeding and/or genetic marker enhanced selection. For example, in one aspect, the method comprises crossing a lettuce plant designated NUN 6109 LTL, or progeny thereof, or a plant comprising all but 1, 2, or 3 or more of the morphological and physiological characteristics of NUN 6109 LTL (e.g. as listed in Table 1), with a different lettuce plant selected from the group consisting of a plant of the same variety, a lettuce plant of a different variety, a (breeding) line, or a wild relative of lettuce (e.g., *L. virosa* or *L. serriola*), and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Dziechciarkova et al, PLANT SOIL ENVIRON., 50, 2004 (2): 47-58). For breeding methods in general see Principles of Plant Genetics and Breeding, 2007, George Acquaah, Blackwell Publishing, ISBN-13: 978-1-4051-3646-4 or Principles of plant breeding, 1960, Allard, John Wiley & Sons, Inc.: Library of Congress Catalog Card Number: 60-14240).

In another aspect the invention provides a method of introducing a single locus conversion or introducing a desired trait into a plant designated NUN 6109 LTL, comprising:

(a) crossing a plant designated NUN 6109 LTL, representative seed of which having been deposited under Accession Number NCIMB 43022, with a second plant comprising a desired single locus to produce F1 progeny plants;
(b) selecting F1 progeny plants that have the single locus; optionally selfing said F1 progeny plant to produce an F2 progeny plant having said single locus;
(c) crossing said F1 or F2 progeny plant of step (a) or step (b), respectively, with a plant of NUN 6109 LTL, representative seed of which having been deposited under Accession Number NCIMB 43022, to produce backcross progeny plants;
(d) selecting backcross progeny plants that have the single locus and one or more (or all) distinguishing characteristics of lettuce according to the invention and/or all the physiological and morphological characteristics of NUN 6109 LTL to produce selected backcross progeny plants; and
(e) optionally repeating steps (c) and (d) one or more times in succession to produce selected second or higher backcross progeny plants that comprise the single locus and otherwise comprise essentially all physiological and morphological characteristics when grown under the same environmental conditions of a plant designated NUN 6109 LTL.

In one embodiment the trait is disease resistance and the resistance is conferred to any race of *Nasonovia ribisnigri*, any race of Downy mildew, Powdery mildew, *Sclerotinia* rot, *Sclerotinia* drop, *Botrytis* (Grey Mold), *Verticillium* Wilt, *Pseudomonas* spp. (Bacterial Soft Rot), Bacterial Leaf Spot, Anthracnose, Bottom rot, Corky root rot, Lettuce mosaic virus, Turnip mosaic virus, Tomato bushy stunt virus (Dieback), Big vein, Cabbage Loopers, Root Aphid, Green Peach Aphid, Lettuce aphid, Pea leafminer, Beet western yellows and aster yellows, *Sclerotinia* minor (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt), lettuce infectious yellows virus (LIYV), lettuce mosaic virus (LMV), Cucumber mosaic virus (CMV), Beet western yellows virus (BWYV), and Alfalfa mosaic virus (AMV).

The invention also provides a lettuce plant comprising at least a first set of the chromosomes of lettuce variety NUN 6109 LTL, a sample of seed of said variety having been deposited under Accession Number NCIMB 43022; optionally further comprising a single locus conversion, wherein said plant has essentially all of the morphological and physiological characteristics of the plant comprising at least a first set of the chromosomes of lettuce NUN 6109 LTL. In another embodiment, this single locus conversion confers a trait selected from the group consisting of male sterility, herbicide tolerance, insect resistance, pest resistance, disease resistance, environmental stress tolerance, modified carbohydrate metabolism and modified protein metabolism.

In one embodiment, NUN 6109 LTL may also be mutated (by e.g. irradiation, chemical mutagenesis, heat treatment, etc.) and mutated seeds or plants may be selected in order to change one or more characteristics of NUN 6109 LTL. Also natural mutants may be identified and used in breeding. Methods such as TILLING and/or EcoTILLING may be applied to lettuce populations in order to identify mutants. Similarly, NUN 6109 LTL may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 6109 LTL, or progeny thereof, by transforming NUN 6109 LTL or progeny thereof with a transgene that confers the desired trait, wherein the transformed plant retains essentially all the morphological and physiological characteristics of NUN 6109 LTL or the progeny thereof and contains the desired trait.

The invention also provides for progeny of lettuce variety NUN 6109 LTL obtained by further breeding with NUN 6109 LTL. In one aspect progeny are F2 progeny obtained by crossing NUN 6109 LTL with another plant or S2 progeny obtained by selfing NUN 6109 LTL. Also encompassed are F3 progeny obtained by selfing the F2 plants.

"Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 6109 LTL when grown under the same environmental conditions. In another embodiment the progeny have one, two, or three distinct traits (qualitative or quantitative) introduced into NUN 6109 LTL, while retaining all the other physiological and morphological characteristics of variety NUN 6109 LTL when grown under the same environmental conditions.

The invention also provides a plant having one, two or three physiological and/or morphological characteristics which are different from those of NUN 6109 LTL and which otherwise has all the physiological and morphological characteristics of NUN 6109 LTL, wherein a representative sample of seed of variety NUN 6109 LTL has been deposited under Accession Number NCIMB 43022. In particular plants which differ from NUN 6109 LTL in none, one, two or three of the characteristics mentioned in Table 1 are encompassed.

In one aspect, the plant having one, two or three physiological and/or morphological characteristics which are different from those of NUN 6109 LTL and which otherwise has all the physiological and morphological characteristics of NUN 6109 LTL differs from NUN 6109 LTL in one, two or three of the distinguishing morphological and/or physiological characteristics selected from 1) average length/width index x10 of fourth leaf; 2) average head weight; 3) average diameter of core at base of head; 4) average core height from base of head to apex; 5) average spread of frame leaves of mature plant; 6) average head size class; 7) average ratio of spread of frame leaves; 8) average undulations of the apical margin of the mature leaf; 9) blistering of the mature leaf.

In another embodiment the plant having one, two or three physiological and/or morphological characteristics which are different from those of NUN 6109 LTL and which otherwise has all the physiological and morphological characteristics of NUN 6109 LTL differs from NUN 6109 LTL in one, two or three morphological or physiological characteristic other than the "distinguishing morphological and/or physiological characteristics" (or essential physiological and/or morphological characteristics) of NUN 6109 LTL selected from: 1) average length/width index x10 of fourth leaf; 2) average head weight; 3) average diameter of core at base of head; 4) average core height from base of head to apex; 5) average spread of frame leaves of mature plant; 6) average head size class; 7) average ratio of spread of frame leaves; 8) average undulations of the apical margin of the mature leaf; 9) blistering of the mature leaf.

Lettuce according to the invention, such as the variety NUN 6109 LTL, or its progeny, or a plant having all physiological and/or morphological characteristics but one, two or three which are different from those of NUN 6109 LTL, can also be reproduced using vegetative reproduction methods. Therefore, the invention provides for a method of producing plants, or a part thereof, of variety NUN 6109 LTL, comprising vegetative propagation of variety NUN 6109 LTL. Vegetative propagation comprises regenerating a whole plant from a plant part of variety NUN 6109 LTL (or from its progeny or from or a plant having all physiological and/or morphological characteristics but one, two or three, which are different from those of NUN 6109 LTL), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets.

The invention also provides for a vegetatively propagated plant of variety NUN 6109 LTL (or from its progeny or from or a plant having all but one, two or three physiological and/or morphological characteristics which are different from those of NUN 6109 LTL, or a part thereof, having one or more distinguishing characteristics and/or all the morphological and physiological characteristics of NUN 6109 LTL (except for the characteristics differing), when grown under the same environmental conditions.

Parts of NUN 6109 LTL (or of its progeny or of a plant having all physiological and/or morphological characteristics but one, two or three which are different from those of NUN 6109 LTL) encompass any cells, tissues, organs obtainable from the seedlings or plants, such as but not limited to: lettuce heads or leaves or parts thereof, cuttings, hypocotyl, cotyledon, pollen, scion and the like. Such parts can be stored and/or processed further. Encompassed are therefore also food or feed products comprising one or more of such parts, such as chopped, sliced, cut, ripped, bagged, preserved, cooked or frozen lettuce heads or leaves from NUN 6109 LTL or from progeny thereof, or from a derived variety, such as a plant having all but one, two or three physiological and/or morphological characteristics which are different from those of NUN 6109 LTL.

In one aspect haploid plants and/or double haploid plants of NUN 6109 LTL, or a plant having all but one, two or three physiological and/or morphological characteristics which are different from those of NUN 6109 LTL, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 6109 LTL (or from its progeny or from a plant having all but one, two or three physiological and/or morphological characteristics which are different from those of NUN 6109 LTL), or from a vegetatively propagated plant of NUN 6109 LTL (or from its progeny or from a plant having all but one, two or three physiological and/or morphological characteristics which are different from those of NUN 6109 LTL), being selected from the group consisting of: harvested lettuce heads or leaves or parts thereof, pollen, cells, fruits or parts thereof, petioles, cotyledons, hypocotyls, shoots or parts thereof, stems or parts thereof, or vines or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

The invention also provides for a food or feed product comprising or consisting of a plant part described herein wherein the plant part can be identified as a part of the plant of the invention. Preferably, the plant part is a lettuce head or leaf or part thereof or another plant part described herein. The food or feed product may be fresh or processed, e.g., chopped, sliced, cut, ripped, bagged, preserved, cooked and/or frozen etc. A plant part can for example be identified by isolating DNA of the plant part and comparing the DNA sequence with that of a plant of NUN 6109 LTL (e.g. by alignment, if at least 99% of the DNA is identical (e.g. 99.5, 99.8 or even 99.9%) then the skilled person will recognize the plant part as a part of NUN 6109 LTL). The skilled person will know how to apply DNA sequence alignment techniques that are known in the art. Alternatively, he may use a set of SNP markers that are unique for NUN 6109 LTL to identify plant parts as part of NUN 6109 LTL.

For example, containers such as cans, boxes, crates, bags, cartons, Modified Atmosphere Packagings, films (e.g. biodegradable films), etc. comprising plant parts of plants (fresh and/or processed) described herein are also provided herein.

Marketable lettuce heads or leaves are generally sorted by size and quality after harvest. Alternatively the lettuce heads or leaves can be sorted by leaf size, shape, texture, glossiness or color.

In a further embodiment a lettuce plant is provided, which (statistically significant) differs from the lettuce plant designated NUN 6109, representative seeds of said lettuce plant having been deposited under accession number NCIMB 43022, in at least one, two, three, four, or five morphological and/or physiological characteristics when grown under the same environmental conditions, whereby the morphological and/or physiological characteristics are those of Table 1. The plant does, thus, not differ in a statistically significant way from NUN 6109 LTL in any of the other morphological and/or physiological characteristics of Table 1 when grown under the same conditions.

Development of NUN 6109

The variety NUN 6109 LTL was developed from an initial cross between two lettuce breeding lines. The female and male parents were crossed to produce hybrid (F1) seeds. After the cross, F1 plants were self-pollinated. From the second to the fifth generation pedigree selection was performed. From the sixth to the ninth generation line selection was performed.

The variety is uniform and genetically stable. This has been established through evaluation of horticultural characteristics. Several seed production events resulted in no observable deviation in genetic stability. The Applicant concluded that NUN 6109 LTL is uniform and stable.

Deposit Information

A total of 2500 seeds of variety NUN 6109 LTL were deposited according to the Budapest Treaty by Nunhems B.V. on Apr. 5, 2018, at the NCIMB Ltd., Ferguson Building, Craibstone Estate, Bucksburn, Aberdeen AB21 9YA, United Kingdom (NCIMB). The deposit has been assigned Accession Number NCIMB 43022. A deposit of NUN 6109 LTL and of the male and female parent line is also maintained at Nunhems B.V. Access to the deposit will be available during the pendency of this application to persons determined by the Director of the U.S. Patent Office to be entitled thereto upon request. Subject to 37 C.F.R. § 1.808 (b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 6109 LTL is GREEN TOWERS, (considered as standard regional check variety), a commercial variety from Harris Moran Co. (Modesto, Calif.) In Table 1 a comparison between NUN 6109 LTL and GREEN TOWERS is shown based on a trial in the USA. Trial location: Acampo, Calif. USA, Planting date: Jan. 20, 2015.

Two replications of 50 plants each, from which 15 plants or plant parts were randomly selected to measure characteristics. In Table 1 the USDA descriptors of NUN 6109 LTL (this application) and reference GREEN TOWERS (commercial variety) are summarized.

TABLE 1

USDA descriptors

| USDA descriptor | NUN 6109 LTL | GREEN TOWERS |
|---|---|---|
| Plant type; 1 = Cutting/Leaf; 2 = Butterhead; 3 = Bibb; 4 = Cos or Romaine; 5 = Great Lakes group; 6 = Vanguard group; 7 = Salinas group; 8 = Eastern group; 9 = Stem; 10 = Latin; 11 = Other (specify) Seed | 4 | 4 |
| Color 1 = white (silver gray), 2 = black (grey brown), 3 = brown Cotyledon to fourth leaf stage | 1 | 1 |
| Shape of Cotyledons 1 = broad, 2 = intermediate, 3 = spatulate | 3 | 3 |
| Shape of fourth leaf 1 = transverse oval; 2 = round; 3 = oval; 4 = elongated; 5 = lanceolate; 6 = pinnately lobed | 4 | 4 |
| Length/width index of fourth leaf (L/W*10) | 26 | 24 |
| Apical margin 1 = entire, 2 = crenate/gnawed, 3 = finely dentate, 4 = moderately dentate, 5 = coarsely dentate, 6 = incised, 7 = lobed, 8 = other (undulate) | 1 | 1 |
| Basal margin 1 = entire, 2 = crenate/gnawed, 3 = finely dentate, 4 = moderately dentate, 5 = coarsely dentate, 6 = incised, 7 = lobed, 8 = other (undulate) | 4 | 4 |
| Undulation 1 = flat, 2 = slight, 3 = medium, 4 = marked | 2 | 2 |
| Green color 1 = yellow green, 2 = light green, 3 = medium green, 4 = dark green | 3 (RHS Yellow Green 144A) | 3 (RHS Yellow Green 146B) |
| Anthocyanin: | | |
| Distribution 1 = absent, 2 = margin only, 3 = spotted, 4 = throughout | 1 | 1 |

TABLE 1-continued

USDA descriptors

| USDA descriptor | NUN 6109 LTL | GREEN TOWERS |
|---|---|---|
| Concentration | NA | NA |
| 1 = light, 2 = moderate, 3 = intense | | |
| Rolling | 1 | 1 |
| 1 = absent, 2 = present | | |
| Cupping | 1 | 1 |
| 1 = uncupped, 3 = markedly | | |
| Reflexing | 1 | 1 |
| 1 = none, 2 = apical margin, 3 = lateral margins | | |
| Mature leaves (harvest mature outer leaves): Margin: | | |
| Incision depth (deepest penetration of the margin) | 1 | 1 |
| 1 = absent/shallow (Dark Green Boston), 2 = moderate (Vanguard), 3 = deep (Great Lakes 659) | | |
| Indentation (finest divisions of the margin) | 2 | 2 |
| 1 = entire, 2 = shallowly dentate (Great Lake 65), 3 = deeply dentate (Great Lake 659) | | |
| Undulations of the apical margin | 3 | 2 |
| 1 = absent/slight (Dark Green Boston), 2 = moderate (Vanguard), 3 = strong (Great Lakes 659) | | |
| Green color | 3 (RHS Yellow Green 146A) | 3 (RHS Yellow Green 146A) |
| 1 = very light green, 2 = light green, 3 = medium green, 4 = dark green, 6 = other | | |
| Anthocyanin: | | |
| Distribution | 1 | 1 |
| 1 = absent, 3 = spotted (California Cream Butter), 4 = throughout (Prize Head) | | |
| Concentration | NA | NA |
| 1 = light, 2 = moderate, 3 = intense | | |
| Size | 2 | 3 |
| 1 = small, 2 = medium, 3 = large | | |
| Glossiness | 2 | 2 |
| 1 = dull, 2 = moderate, 3 = glossy | | |
| Blistering | 3 | 2 |
| 1 = absent/slight, 2 = moderate, 3 = strong | | |
| Leaf thickness; 1 = thin, 2 = intermediate, 3 = thick | 3 | 3 |
| Trichomes; 1 = absent, 2 = present | 1 | 1 |
| Plant | | |
| Spread of frame leaves | 31 cm | 42 cm |
| Head diameter | NA | NA |
| Head shape | 5 | 5 |
| 1 = flattened, 4 = elongate, 5 = non-heading | | |
| Head size class | 2 | 3 |
| 1 = small, 2 = medium, 3 = large | | |
| Head per carton | nr | nr |
| Head weight | 594 g | 673 g |
| Head firmness | 1 | 1 |
| 1 = loose, 3 = Firm, 4 = very firm | | |
| Butt | | |
| Shape | 3 | 3 |
| 1 = slightly concave, 2 = flat, 3 = rounded | | |
| Midrib | 2 | 2 |
| 1 = Flattened, 2 = Moderately Raised, 3 = prominently raised | | |
| Core | | |
| Diameter at base of head | 28 mm | 34 mm |
| Ratio of spread of frame leave | 1.1 | 1.2 |
| Core height from base of head to apex | 43 | 62 |
| Bolting (first water date:) | nr | nr |
| Maturity (earliness of harvest-mature head formation) Location: Acampo, CA; planting date: 20 Jan. 2015 | | |
| Winter | 74 | 72 |
| Adaptation: 0 = not tested, 1 = not adapted, 2 = adapted | | |
| Primary regions of adaptation | | |
| Southwest (CA and/or AZ desert) | 2 | |
| West coast | 2 | |
| Northeast | 0 | |
| North Central | 0 | |
| Southeast | 0 | |
| Season | | |
| Spring | 2 (Area West Coast) | nr |
| Summer | 2 (Area West Coast) | nr |
| Fall | 2 (Area West Coast) | nr |
| Winter | 2 (Area West Coast) + Southwest) | nr |
| Greenhouse | nr | nr |
| Soil type | 3 | 3 |
| 1 = mineral, 2 = organic, 3 = both | | |

These are typical values. Values may vary due to environment. Other values that are substantially equivalent are also within the scope of the invention.
N.A. = not applicable; n.r. = not recorded.

TABLE 2 other descriptors

| Other descriptor | NUN 6109 LTL | GREEN TOWERS |
|---|---|---|
| Fourth leaf length | 59.4 mm | 53.9 mm |
| Fourth leaf width | 25 mm | 22.6 mm |
| Mature plant height | 22.1 cm | 32.7 cm |

The invention claimed is:

1. A whole plant, a plant part or a seed of lettuce variety NUN 6109 LTL, wherein a representative sample of said seed has been deposited under Accession Number NCIMB 43022.

2. A whole plant or part thereof grown from the seed of claim 1.

3. The plant part of claim 2, further defined as a leaf, head, pollen, stem, an ovule, a fruit, a scion, a rootstock, cutting, flower or a part of any of these or a cell.

4. A whole lettuce plant, which does not differ at the level of 5% when grown under the same environmental conditions from lettuce variety NUN 6109 LTL of claim 2, or a part of said whole lettuce plant.

5. A tissue or cell culture of regenerable cells of lettuce variety NUN 6109 LTL of claim 2.

6. The tissue or cell culture according to claim 5, comprising cells or protoplasts from a plant part selected from the group consisting of embryos, meristems, cotyledons, hypocotyl, pollen, leaves, anthers, roots, root tips, pistil, petiole, flower, fruit, seed, stem and stalks.

7. A lettuce plant regenerated from the tissue or cell culture of claim 5, wherein the plant has all of the physiological and morphological characteristics of the plant of lettuce variety NUN 6109 LTL, wherein a representative sample of seed of said variety has been deposited under Accession Number NCIMB 43022, where numerical values are determined at the 5% level when grown under the same environmental conditions.

8. A method of producing of lettuce variety NUN 6109 LTL of claim 2, or a part thereof, comprising vegetative propagation of said variety.

9. The method of claim 8, wherein said vegetative propagation comprises regenerating a whole plant from a part of lettuce variety NUN 6109 LTL, wherein a representative sample of seed of said variety has been deposited under Accession Number NCIMB 43022.

10. The method of claim 8, wherein said part is a cutting, a cell culture or a tissue culture.

11. A vegetative propagated plant propagated from the plant part of lettuce variety NUN 6109 LTL of claim 2, wherein the propagated plant has all of the physiological and morphological characteristics of the plant of claim 2 when determined at the 5% level for plants grown under the same environmental conditions.

12. A method of producing a lettuce plant, comprising crossing the plant of claim 2 with a second lettuce plant.

13. The method of claim 12 further comprising a step of selecting first generation progeny from said crossing.

14. The method of claim 13 further comprising a step of allowing the first generation progeny to form seed.

15. A first generation progeny of the lettuce variety NUN 6109 LTL of claim 2 obtained by further breeding with said variety.

16. A food or feed product comprising the plant part of claim 3.

17. A lettuce plant comprising at least a first set of the chromosomes of lettuce variety NUN 6109 LTL of claim 2.

* * * * *